United States Patent
Knott et al.

(10) Patent No.: US 11,229,729 B2
(45) Date of Patent: Jan. 25, 2022

(54) DEVICE FOR ESTABLISHING THE VENOUS INFLOW TO A BLOOD RESERVOIR OF AN EXTRACORPOREAL BLOOD CIRCULATION SYSTEM

(71) Applicant: LivaNova Deutschland GmbH, Munich (DE)

(72) Inventors: Erwin Knott, Poing (DE); Johann Schreyer, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 518 days.

(21) Appl. No.: 16/180,870

(22) Filed: Nov. 5, 2018

(65) Prior Publication Data
US 2019/0070353 A1    Mar. 7, 2019

Related U.S. Application Data

(62) Division of application No. 13/322,844, filed as application No. PCT/EP2010/055522 on Apr. 26, 2010, now abandoned.

(30) Foreign Application Priority Data

May 29, 2009 (DE) .......................... 102009026592.9

(51) Int. Cl.
*A61M 1/36* (2006.01)
(52) U.S. Cl.
CPC ........ *A61M 1/3621* (2013.01); *A61M 1/3667* (2014.02); *A61M 1/3627* (2013.01); *A61M 1/3663* (2013.01); *A61M 2205/3389* (2013.01)

(58) Field of Classification Search
CPC .................................................. A61M 1/3621
See application file for complete search history.

(56) References Cited

U.S. PATENT DOCUMENTS

| | | | |
|---|---|---|---|
| 3,551,072 A | 12/1970 | Zimmerly | |
| 3,588,589 A | 6/1971 | Vonk | |
| 3,588,859 A | 6/1971 | Petree | |

(Continued)

FOREIGN PATENT DOCUMENTS

| | | | |
|---|---|---|---|
| CN | 86103696 A | 1/1987 | |
| CN | 1147964 A | 4/1997 | |

(Continued)

OTHER PUBLICATIONS

Catalog of Products, 2009 Terumo Europe Cardiovascular Systems, 142 pages.

(Continued)

*Primary Examiner* — Catharine L Anderson
*Assistant Examiner* — Arjuna P Chatrathi
(74) *Attorney, Agent, or Firm* — Seager, Tufte & Wickhem LLP.

(57) ABSTRACT

A device for establishing venous inflow to a blood reservoir of an extracorporeal blood circulation system includes a restricting unit for gradually closing a venous inflow line and a vacuum unit for supplying vacuum to the blood reservoir. The device includes a control unit that supplies a first actuating signal to the restricting unit for restricting venous inflow to the blood reservoir and supplies a second actuating signal to the vacuum unit for establishing a degree of vacuum within the blood reservoir.

16 Claims, 4 Drawing Sheets

(56) References Cited

U.S. PATENT DOCUMENTS

| | | |
|---|---|---|
| 3,851,181 A | 11/1974 | Heule |
| 3,927,980 A | 12/1975 | Leonard |
| 4,006,745 A | 2/1977 | Sorenson et al. |
| 4,170,765 A | 10/1979 | Austin et al. |
| 4,177,649 A | 12/1979 | Venema |
| 4,193,004 A | 3/1980 | Anderson et al. |
| 4,275,726 A | 6/1981 | Schael |
| 4,309,871 A | 1/1982 | Venema |
| 4,374,088 A | 2/1983 | Stenberg et al. |
| 4,464,164 A * | 8/1984 | Troutner ............... A61M 1/30 128/DIG. 3 |
| 4,466,804 A | 8/1984 | Hino |
| 4,490,331 A | 12/1984 | Steg, Jr. |
| 4,518,318 A | 5/1985 | Jensen et al. |
| 4,530,696 A | 7/1985 | Bisera et al. |
| 4,599,093 A | 7/1986 | Steg, Jr. |
| 4,602,344 A | 7/1986 | Ferretti et al. |
| 4,642,089 A | 2/1987 | Zupkas et al. |
| 4,664,682 A | 5/1987 | Monzen |
| 4,678,404 A | 7/1987 | Lorett et al. |
| 4,701,101 A | 10/1987 | Sapoff |
| 4,705,497 A | 11/1987 | Shitaokoshi et al. |
| 4,782,451 A | 11/1988 | Mazzarella et al. |
| 4,828,543 A | 5/1989 | Weiss et al. |
| 4,846,800 A | 7/1989 | Ouriel et al. |
| 4,876,066 A | 10/1989 | Bringham et al. |
| 4,955,874 A | 9/1990 | Farrar et al. |
| 4,984,462 A | 1/1991 | Hass et al. |
| 4,991,433 A | 2/1991 | Warnaka et al. |
| 5,039,430 A | 8/1991 | Corey, Jr. |
| 5,039,482 A | 8/1991 | Panzani et al. |
| 5,043,707 A | 8/1991 | Heinze |
| 5,049,146 A | 9/1991 | Bringham et al. |
| 5,055,198 A | 10/1991 | Shettigar |
| 5,060,512 A | 10/1991 | Kanashige et al. |
| 5,061,236 A | 10/1991 | Sutherland et al. |
| 5,078,677 A | 1/1992 | Gentelia et al. |
| 5,110,549 A | 5/1992 | Gordon |
| 5,112,480 A | 5/1992 | Hukasawa |
| 5,120,303 A | 6/1992 | Hombrouckx |
| 5,135,485 A | 8/1992 | Cohen et al. |
| 5,147,187 A | 9/1992 | Ito et al. |
| 5,149,318 A | 9/1992 | Lindsay |
| 5,158,533 A | 10/1992 | Strauss et al. |
| 5,178,603 A | 1/1993 | Prince |
| 5,186,431 A * | 2/1993 | Tamari ................... F16K 7/07 251/5 |
| 5,215,519 A | 6/1993 | Shettigar |
| 5,226,265 A | 7/1993 | Kelly et al. |
| 5,240,380 A | 8/1993 | Mabe |
| 5,266,265 A | 11/1993 | Raible |
| 5,270,005 A | 12/1993 | Raible |
| 5,282,783 A | 2/1994 | Lindsay |
| 5,303,585 A | 4/1994 | Lichte |
| 5,304,164 A | 4/1994 | Lindsay |
| 5,318,510 A | 6/1994 | Cathcart |
| 5,399,074 A | 3/1995 | Nose et al. |
| 5,403,273 A | 4/1995 | Lindsay |
| 5,411,705 A | 5/1995 | Thor et al. |
| 5,458,566 A | 10/1995 | Herrig et al. |
| 5,458,567 A | 10/1995 | Cathcart |
| 5,458,579 A | 10/1995 | Chodorow et al. |
| 5,563,490 A | 10/1996 | Kawaguchi et al. |
| 5,563,584 A | 10/1996 | Rader et al. |
| 5,586,085 A | 12/1996 | Lichte |
| 5,591,399 A | 1/1997 | Goldman et al. |
| 5,604,315 A | 2/1997 | Briefer et al. |
| 5,619,993 A | 4/1997 | Lee |
| 5,645,540 A * | 7/1997 | Henniges ............ A61M 1/0023 604/320 |
| 5,667,485 A | 9/1997 | Lindsay |
| 5,725,357 A | 3/1998 | Nakazeki et al. |
| 5,756,940 A | 5/1998 | Van et al. |
| 5,770,073 A | 6/1998 | Bach et al. |
| 5,775,879 A | 7/1998 | Durando |
| 5,800,721 A | 9/1998 | McBride |
| 5,823,045 A | 10/1998 | Van et al. |
| 5,826,576 A | 10/1998 | West |
| 5,849,186 A | 12/1998 | Raneri et al. |
| 5,928,180 A | 7/1999 | Krivitski et al. |
| 5,955,672 A | 9/1999 | Van et al. |
| 6,017,493 A * | 1/2000 | Cambron ............... A61M 1/36 422/44 |
| 6,048,363 A | 4/2000 | Nagyszalanczy et al. |
| 6,123,519 A | 9/2000 | Kato et al. |
| 6,146,411 A | 11/2000 | Noda et al. |
| 6,164,325 A | 12/2000 | Braun |
| 6,287,270 B1 | 9/2001 | Fini |
| 6,337,049 B1 | 1/2002 | Tamari |
| 6,345,214 B1 | 2/2002 | Dulphy-Vigor et al. |
| 6,475,176 B2 | 11/2002 | Fini |
| 6,542,848 B1 | 4/2003 | Neeser et al. |
| 6,562,012 B1 | 5/2003 | Brown et al. |
| 6,564,627 B1 | 5/2003 | Sabini et al. |
| 6,592,340 B1 | 7/2003 | Horo et al. |
| 6,631,639 B1 | 10/2003 | Dam et al. |
| 6,652,495 B1 | 11/2003 | Walker |
| 6,694,570 B2 | 2/2004 | Chen |
| 6,770,048 B2 | 8/2004 | Fini |
| 6,931,926 B1 | 8/2005 | Van Ee |
| 7,072,769 B2 | 7/2006 | Fletcher-Haynes et al. |
| 7,147,614 B2 | 12/2006 | Fini |
| 7,591,812 B1 | 9/2009 | Tamari |
| 7,694,570 B1 | 4/2010 | Dam et al. |
| 7,982,612 B2 | 7/2011 | Braun |
| 8,105,265 B2 | 1/2012 | Demers et al. |
| 8,394,321 B2 | 3/2013 | Franzoni et al. |
| 8,409,124 B2 | 4/2013 | Steffens et al. |
| 8,500,673 B2 | 8/2013 | Zanotti et al. |
| 8,506,513 B2 | 8/2013 | Rossi et al. |
| 8,734,376 B2 | 5/2014 | Simpson et al. |
| 9,011,769 B2 | 4/2015 | Silvestri et al. |
| 10,213,541 B2 | 2/2019 | Silvestri et al. |
| 10,458,833 B2 | 10/2019 | Rossi |
| 2001/0013822 A1 | 8/2001 | Nazarian et al. |
| 2001/0050256 A1 | 12/2001 | Krivitski |
| 2002/0032399 A1 | 3/2002 | Fini |
| 2002/0033181 A1 | 3/2002 | Groth et al. |
| 2002/0038392 A1 | 3/2002 | De La Huerga |
| 2002/0085952 A1 * | 7/2002 | Ellingboe ............ A61M 1/3632 422/45 |
| 2002/0094300 A1 | 7/2002 | Yokoyama et al. |
| 2002/0128582 A1 | 9/2002 | Farrell et al. |
| 2002/0133066 A1 | 9/2002 | Miller et al. |
| 2003/0033871 A1 | 2/2003 | Carroll et al. |
| 2003/0035730 A1 | 2/2003 | Schob |
| 2003/0045772 A1 | 3/2003 | Reich et al. |
| 2003/0139643 A1 | 7/2003 | Smith et al. |
| 2003/0144646 A1 | 7/2003 | Se et al. |
| 2003/0163078 A1 * | 8/2003 | Fallen ................ A61M 1/3666 604/6.01 |
| 2003/0175151 A1 | 9/2003 | Ghelli et al. |
| 2004/0047737 A1 | 3/2004 | Nose et al. |
| 2004/0064292 A1 | 4/2004 | Beck et al. |
| 2004/0152944 A1 | 8/2004 | Medvedev et al. |
| 2005/0025630 A1 | 2/2005 | Ayre et al. |
| 2005/0119600 A1 | 6/2005 | Lucke et al. |
| 2005/0230313 A1 | 10/2005 | O'Mahony et al. |
| 2006/0015056 A1 | 1/2006 | Ellingboe et al. |
| 2006/0089695 A1 | 4/2006 | Bolea et al. |
| 2006/0092360 A1 | 5/2006 | Hong |
| 2006/0122558 A1 * | 6/2006 | Sherman ............ A61M 1/0031 604/67 |
| 2006/0150596 A1 | 7/2006 | Takahashi et al. |
| 2006/0167400 A1 | 7/2006 | Ellingboe et al. |
| 2006/0226087 A1 | 10/2006 | Robinson et al. |
| 2006/0260392 A1 | 11/2006 | Hedrick |
| 2006/0277269 A1 | 12/2006 | Dent et al. |
| 2007/0017518 A1 | 1/2007 | Farrugia et al. |
| 2007/0110612 A1 | 5/2007 | Ito |
| 2007/0142923 A1 | 6/2007 | Ayre et al. |
| 2007/0194981 A1 | 8/2007 | Hagg et al. |
| 2007/0209662 A1 | 9/2007 | Bowen et al. |
| 2008/0027368 A1 | 1/2008 | Kollar et al. |

(56) References Cited

U.S. PATENT DOCUMENTS

| | | |
|---|---|---|
| 2008/0078382 A1 | 4/2008 | Lemahieu et al. |
| 2008/0171960 A1 | 7/2008 | Brieske et al. |
| 2008/0245530 A1 | 10/2008 | Kuzmichev |
| 2008/0275377 A1 | 11/2008 | Paolini et al. |
| 2009/0012443 A1 | 1/2009 | Ghelli et al. |
| 2009/0099498 A1 | 4/2009 | Demers et al. |
| 2009/0149950 A1 | 6/2009 | Wampler |
| 2010/0042038 A1 | 2/2010 | Urdahl et al. |
| 2010/0140182 A1 | 6/2010 | Chapman et al. |
| 2010/0275953 A1 | 11/2010 | Orue et al. |
| 2010/0280430 A1 | 11/2010 | Caleffi et al. |
| 2011/0098625 A1 | 4/2011 | Masala et al. |
| 2011/0257576 A1 | 10/2011 | Simpson et al. |
| 2011/0257578 A1 | 10/2011 | Zanotti et al. |
| 2011/0257579 A1 | 10/2011 | Rossi et al. |
| 2012/0067133 A1 | 3/2012 | Waldrop et al. |
| 2012/0130299 A1 | 5/2012 | Knott et al. |
| 2012/0226446 A1 | 9/2012 | Nelson et al. |
| 2013/0017119 A1 | 1/2013 | Silvestri et al. |
| 2013/0303965 A1 | 11/2013 | Rossi et al. |
| 2013/0331758 A1 | 12/2013 | Meibaum et al. |
| 2014/0278156 A1 | 9/2014 | Thompson et al. |
| 2015/0100253 A1 | 4/2015 | Austerlitz et al. |
| 2015/0196703 A1 | 7/2015 | Silvestri et al. |
| 2015/0367120 A1 | 12/2015 | Kusters et al. |
| 2017/0089746 A1 | 3/2017 | Rossi |
| 2019/0167886 A1 | 6/2019 | Silvestri et al. |

FOREIGN PATENT DOCUMENTS

| | | |
|---|---|---|
| CN | 1197677 A | 11/1998 |
| CN | 1458851 A | 11/2003 |
| DE | 2455229 A1 | 5/1976 |
| DE | 2754894 A1 | 6/1979 |
| DE | 3935502 A1 | 5/1991 |
| DE | 19840399 A1 | 3/1999 |
| DE | 102004040441 A1 | 6/2006 |
| DE | 102005001779 A1 | 9/2006 |
| DE | 102005029682 A1 | 12/2006 |
| DE | 102007026010 B4 | 11/2010 |
| EP | 0371173 A1 | 6/1990 |
| EP | 0587251 A1 | 3/1994 |
| EP | 0472480 B1 | 8/1995 |
| EP | 0820775 A2 | 1/1998 |
| EP | 0952433 A1 | 10/1999 |
| EP | 1053760 A2 | 11/2000 |
| EP | 1070509 A2 | 1/2001 |
| EP | 0690730 B1 | 5/2002 |
| EP | 1210956 A2 | 6/2002 |
| EP | 1003575 B1 | 10/2004 |
| EP | 0766974 B1 | 9/2006 |
| EP | 2754458 A2 | 7/2014 |
| EP | 2435106 B1 | 11/2014 |
| EP | 2842584 A1 | 3/2015 |
| FR | 2811752 A1 | 1/2002 |
| GB | 2009862 A | 6/1979 |
| GB | 2109934 A | 6/1983 |
| JP | 56-023960 A | 3/1981 |
| JP | 57-500411 A | 3/1982 |
| JP | 62-258671 A | 11/1987 |
| JP | 03-091352 | 9/1991 |
| JP | 08-019602 A | 1/1996 |
| JP | 08-506982 A | 7/1996 |
| JP | 11-506701 A | 6/1999 |
| JP | 2944749 B2 | 9/1999 |
| JP | 2000-000299 A | 1/2000 |
| JP | 2001-503665 A | 3/2001 |
| JP | 2001-204815 A | 7/2001 |
| JP | 2001-514939 A | 9/2001 |
| JP | 2001-523339 A | 11/2001 |
| JP | 2002-165878 A | 6/2002 |
| JP | 2002-336348 A | 11/2002 |
| JP | 2003-052717 A | 2/2003 |
| JP | 2003-126246 A | 5/2003 |
| JP | 2005-066013 A | 3/2005 |
| JP | 2006-025531 A | 1/2006 |
| JP | 2006-325750 A | 12/2006 |
| JP | 2007-130290 A | 5/2007 |
| JP | 2008-000597 A | 1/2008 |
| JP | 2008-194386 A | 8/2008 |
| JP | 2008-270595 A | 11/2008 |
| JP | 2009-240428 A | 10/2009 |
| JP | 2009-287593 A | 12/2009 |
| JP | 2011-076394 A | 4/2011 |
| WO | 94/21311 A2 | 9/1994 |
| WO | 96/24397 A2 | 8/1996 |
| WO | 97/33672 A1 | 9/1997 |
| WO | 98/20957 A1 | 5/1998 |
| WO | 98/48868 A1 | 11/1998 |
| WO | 99/08734 A1 | 2/1999 |
| WO | 99/65413 A1 | 12/1999 |
| WO | 00/15154 A1 | 3/2000 |
| WO | 00/44415 A1 | 8/2000 |
| WO | 01/47442 A1 | 7/2001 |
| WO | 01/76656 A2 | 10/2001 |
| WO | 02/39931 A1 | 5/2002 |
| WO | 02/39933 A1 | 5/2002 |
| WO | 02/95675 A1 | 11/2002 |
| WO | 03/26724 A1 | 4/2003 |
| WO | 2006/021295 A1 | 3/2006 |
| WO | 2006/057650 A2 | 6/2006 |
| WO | 2006/122282 A2 | 11/2006 |
| WO | 2007/018513 A1 | 2/2007 |
| WO | 2008/119993 A1 | 10/2008 |
| WO | 2009/144522 A1 | 12/2009 |
| WO | 2010/041604 A1 | 4/2010 |
| WO | 2014/041604 A1 | 3/2014 |

OTHER PUBLICATIONS

Definition of "Cylinder", downloaded from http://dictionary.reference.com/browse/cylinder, download on Apr. 28, 2014, 3 pages.

European Search Report and Search Opinion Received for EP Application No. 14164506.9, dated Sep. 19, 2014, 10 pages.

European Search Report issued in EP Application No. 11173655, completed Nov. 30, 2011, 9 pages.

Extended European Search Report issued in 14188440.3, dated Jan. 30, 2015, 7 pages.

Fischer, Gerhard, Betriebsmesstechnik, unveranderte Auflage, VEB Verlag Technik Berlin, 1986, 3 pages (machine translations: Business measuring technique, unchanged edition).

Henriksen Kerm et al., "Envisioning Patient Safety in the Year 2025: Eight Perspectives", Advances in Patient Safety: New Directions and Alternative Approaches, Agency for Healthcare Research and Quality, vol. 1, Aug. 2008.

International Preliminary Report on Patentability issued in PCT/IB2014/061491 dated Dec. 1, 2016, 12 pages.

International Preliminary Report on Patentability received for PCT Patent Application No. PCT/IB2011/051639, dated Nov. 1, 2012, 10 pages.

International Preliminary Reporton Patentability received for PCT Patent Application No. PCT/IB2012/053497, dated Jan. 23, 2014, 10 pages.

International Preliminary Reporton Patentability, Chapter II, issued in PCT/EP2010/055522, (with translation) dated May 31, 2011, 13 pages.

International Search Report and Written Opinion issued in PCT/EP2010/055522, (with translation) dated Aug. 6, 2010, 10 pages.

International Search Report and Written Opinion issued in PCT/IB2011/051639, dated Nov. 18, 2011, 15 pages.

International Search Report and Written Opinion issued in PCT/IB2014/061491, dated Mar. 6, 2015, 16 pages.

International Search Report and Written Opinion received for PCT Patent Application No. PCT/IB2012/053497, dated Nov. 15, 2012, 12 pages.

Klonoff, David C., "Designing an Artificial Pancreas System to be Compatible with Other Medical Devices", Journal of Diabetes Science and Technology, vol. 2, No. 5, Sep. 2008, pp. 741-745.

(56) References Cited

OTHER PUBLICATIONS

Terumo Europe Cardiovascular Systems, Innovative Products for the Treatment of Cardiovascular Disease, 2006 Terumo Europe, 105 pages.
Van der Togt, Remko et al., "Electromagnetic Interference From Radio Frequency Identification Inducing Potentially Hazardous Incidents in Critical Care medical Equipment", JAMA, Jun. 25, 2008, vol. 299, No. 24, 7 pages.
Weber, Tim, "Talking Barcodes that Change our Lives", BBC News, published Apr. 48, 2004, 3 pages.
Wikipedia."Fullstandmessung" [online]. Retrieved from https://de.wikipedia.org/w/index.php?title=F%C3%BCllstandmessung&oldid=69998631, last modified Jan. 30, 2010. Engiish translation retreived from https://en.wikipedia.org/wiki/Level_sensor, Oct. 18, 2016.

\* cited by examiner

DEVICE FOR ESTABLISHING THE VENOUS INFLOW TO A BLOOD RESERVOIR OF AN EXTRACORPOREAL BLOOD CIRCULATION SYSTEM

CROSS-REFERENCE TO RELATED APPLICATIONS

The present application is a division of U.S. application Ser. No. 13/322,844, filed Feb. 7, 2012, which is a national phase application of PCT/EP2010/055522, filed pursuant to 35 U.S.C. § 371, which claims priority to DE 10 2009 02 6592.9, filed May 29, 2009. All applications are incorporated herein by reference in their entireties.

TECHNICAL FIELD

The invention relates to a device for establishing venous inflow to a blood reservoir in an extracorporeal blood circulation system.

BACKGROUND

An extracorporeal blood circulation system often includes, in addition to other components, a venous inflow line from a patient to a blood reservoir, for example a venous cardiotomy reservoir for blood and/or priming solution, and an arterial inflow line from the reservoir to the patient. In order to convey blood from the patient into the reservoir, the reservoir is located at a lower level than the patient so that drainage can already occur by means of gravity. Using a blood pump, usually a roller pump, the blood is conveyed out of the reservoir through the arterial inflow line and is delivered to the patient.

So that the venous inflow to the reservoir occurs to a sufficient extent, large tube cross-sections are required in the case of pure gravitational drainage, which is problematic in respect of the strain on the patient which is associated with the drainage line. Furthermore, pure gravitational drainage is unfavorable as regards the ability to influence the venous inflow amount since in order to do so, the difference in height between the reservoir and the patient would have to be altered while maintaining the extracorporeal blood circulation.

As is described, for example, in WO 00/44415 A, it has already been proposed to apply a vacuum to the reservoir in order to reduce the cross-section of the drainage line and to be able to influence the venous inflow. In this regard, WO 00/44415 A discloses a vacuum regulator that simplifies management of the vacuum by the user so as to increase patient safety during an operation. The reason for this is that a reliable regulation of the vacuum first of all enables a simple adjustment of the vacuum by a user and thus a simple adjustment of the venous inflow. A reliable regulation of the vacuum also prevents a vacuum which is too high and which presents a danger to the patient, whereby it must be noted that the withdrawal of the blood from the reservoir using the blood pump which arterially supplies the blood to the patient contributes to the creation and/or increase of the vacuum. In WO 00/44415 A, previously known solutions are referred to as being insufficient and an independent device for regulating the vacuum is described, which reliably regulates the vacuum in the reservoir and optionally also reduces it should this be necessary.

When supplying blood from the reservoir to the patient, care must be taken to ensure that no more blood is removed from the reservoir than is present therein or is supplied thereto. The user must therefore make sure that there is a sufficient minimum amount in the reservoir and additionally coordinate the inflow and outflow such that sufficient amounts are built up in the reservoir but are also supplied to the patient since a physiologically sufficient supply of the patient must always be ensured in an extracorporeal blood circulation system. The user may thereby, for example, increase or reduce the delivery rate of the roller pump or he may reduce the line cross-section of the supply line by means of clamping and/or increase it again. In addition, the user must pay attention to the amount of drained blood and suitably adjust the vacuum in the reservoir—even in the aforementioned vacuum regulator. The user must meet this requirement in an environment which furthermore compels him, in all of his actions, to pay attention to the surgical operation supported by the extracorporeal circulation. Overall, the adjustment of the venous inflow amount to the reservoir of an extracorporeal blood circulation system therefore occurs in a stressful working environment, and thus the previous technical solutions for supporting the user in the adjustment of the venous inflow amount to the reservoir must be regarded as sub-optimal.

Against this background, the technical problem to be solved by the invention is to specify a device for establishing the venous inflow to a blood reservoir of an extracorporeal blood circulation system, which further simplifies the management of the extracorporeal blood circulation system for the user.

SUMMARY

A device as according to the invention for establishing the venous inflow to a blood reservoir of an extracorporeal blood circulation system, which includes a venous inflow line from a patient to the reservoir and an arterial inflow line from the reservoir to the patient, further includes, in addition to a restricting unit for gradually closing, in particular clamping, the venous inflow line in order to restrict the venous inflow amount to the reservoir and a vacuum unit for applying a vacuum to the reservoir in order to increase the venous inflow amount to the reservoir, a control means which supplies to the restricting unit a first actuating signal for establishing the degree of closure of the venous inflow line in order to determine the extent of the restriction of the venous inflow amount to the reservoir, and which supplies to the vacuum unit a second actuating signal for establishing the amount of vacuum in the reservoir in order to determine the extent of the increase in the venous inflow amount to the reservoir, and which includes a single operating element for setting of the amount of venous inflow to the reservoir by a user.

By providing a single operating element for setting of the amount of venous inflow to the reservoir by a user, the user is given the opportunity in a simple manner to determine the venous inflow to the reservoir at, above and below a basic value by a single adjustment process. The basic value is set by restricting conveyance in the case of venous inflow amounts below this value and by actively supporting conveyance of the inflow amount, which is otherwise conveyed and defined by gravity, in the case of venous inflow amounts above this value. As a result of the configuration of the control means according to the invention, it is achieved that the device according to the invention appropriately adjusts and regulates the venous inflow. It should be noted that the single operating element described above and in the following is solely for the function of setting the amount of venous inflow to the reservoir by a user. The control means can additionally include further operating elements, such as, for example, an on/off switch, a brightness regulator for optionally provided displays, a selector switch for activating/deactivating an alarm, etc. However, according to some embodiments of the invention, only one single operating element is provided for setting of the amount of venous inflow to the reservoir by a user, said element allowing setting of the venous inflow both at above and below a basic value.

In some embodiments, the control means includes a display device for visual display of a display value corresponding to the amount of venous inflow. By means of this display, an indication of value as regards the venous inflow, the vacuum in the reservoir and/or the amount of blood stored in the reservoir can be displayed to the user.

In some embodiments, the vacuum unit is connected to a vacuum source via a line or alternatively or additionally includes an integrated vacuum source, in particular a pump.

In some embodiments, a vacuum sensor for detecting the vacuum in the reservoir is provided, which is connected to the control means for providing a corresponding measuring signal.

In some embodiments, a level sensor for detecting the level of blood present in the reservoir is provided, which is connected to the control means for providing a corresponding measuring signal.

In some embodiments, an arterial inflow amount sensor for detecting the inflow amount conveyed in the arterial inflow line is provided, which is connected to the control means for providing a corresponding measuring signal.

In some embodiments, the control means generates a third actuating signal which establishes the delivery rate of a blood pump such that the arterial inflow amount can at least be influenced.

In some embodiments, the single operating element is configured for specifying an amount of blood to be stored in a reservoir so that the venous inflow to the reservoir can be set in this manner.

In some embodiments, the vacuum unit includes a safety device which, upon actuation by the control means or if control should fail, interrupts the application of a vacuum to the reservoir and establishes atmospheric pressure in the reservoir.

BRIEF DESCRIPTION OF THE FIGURES

The invention will be described in more detail in the following with reference to the drawings, in which.

DETAILED DESCRIPTION

Figure 1:
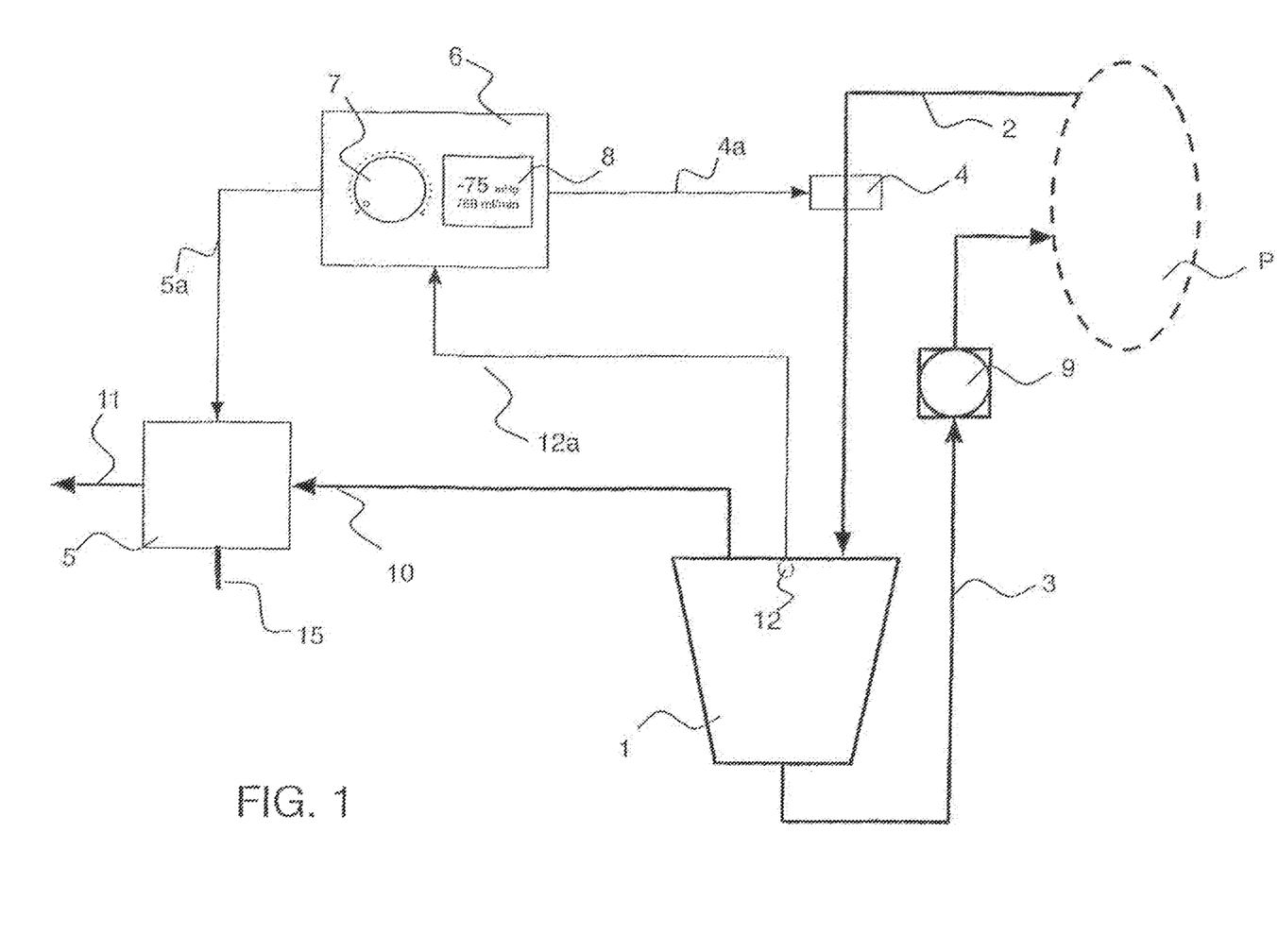
FIG. 1 shows a view of the basic structure of an extracorporeal blood circulation system having a device according to a first embodiment of the invention.

As is shown in FIG. 1 by means of a first embodiment of a device according to the invention, an extracorporeal blood circulation system basically includes, in addition to a reservoir 1, a venous inflow line 2 from a patient P to the reservoir 1 and an arterial inflow line 3 from the reservoir 1 to the patient P. In order to supply blood from the reservoir 1 to the patient P, a pump 9, such as a roller pump or a centrifugal pump, is provided on or in the arterial inflow line 3. As is apparent from FIG. 1, the reservoir 1 is located at a lower level than the patient so that a venous inflow to the reservoir is already possible owing to gravity alone, the extent of which also depends, however, on the cross-section of the tube used in the venous inflow.

In order to restrict the venous inflow to the reservoir 1, the first embodiment of the invention as described herein includes a restricting unit 4, by which the venous inflow line 2 can be gradually closed, for example by clamping or squeezing. For this purpose, the restricting unit 4 includes an electromagnetically, pneumatically or hydraulically-operated clamp which is not shown in detail in FIG. 1. The restricting unit 4 is arranged on the venous inflow line 2 and in some embodiments acts externally on the tube without coming into contact with the blood.

In order to increase the venous inflow to the reservoir 1, the first embodiment of a device according to the invention includes a vacuum unit 5 for applying a vacuum to the reservoir 1. For this purpose, the vacuum unit 5 is connected via a vacuum line 10 to the reservoir 1 which is accordingly designed so as to be pressure-tight. If the vacuum unit 5 is itself not configured for generating the vacuum, for example by integration of a suitable pump, the vacuum unit 5, as is the case in the first embodiment shown in FIG. 1, is connected to a vacuum source via a vacuum source line 11. Suitable vacuum sources are generally available in the form of stationary installations in hospitals where the device according to the invention is primarily used.

According to the invention, the setting of the venous inflow by the user occurs in a simple and comfortable yet also safe manner via a control means 6 which is shown in FIG. 1. The control means 6 supplies to the restricting unit 4, via a first actuation line 4a, a first actuating signal for establishing the degree of closure of the venous supply line 2 in order to carry out restriction of the venous inflow amount to the reservoir. The control means 6 furthermore supplies to the vacuum unit 5, via a second actuation line 5a, a second actuating signal for establishing the amount of vacuum in the reservoir 1 in order to carry out an increase in the venous inflow amount to the reservoir.

According to the invention, the control means 6 includes a single operating element 7 for setting of the amount of venous inflow to the reservoir by a user of the device. Solely by actuating this single operating element 7, the user can set the venous inflow amount to the reservoir 1 and thereby undertake both an increase to beyond the amount which is essentially determined by the gravitational drainage and the cross-section of the tube used on the venous side, as well as a reduction to below this value. The control means 6 according to the invention converts the setting carried out by the user by means of the single operating element 7 into a corresponding actuation of the restricting unit 4 or the vacuum unit 5 so as to thereby cause a reduction of the venous inflow amount by closing (clamping) the venous inflow tube line 2 or an increase in the venous inflow amount by creating a vacuum in the reservoir 1.

As is shown by FIG. 1, the first embodiment includes a pressure sensor 12, which is arranged on or in the reservoir 1 so as to detect the vacuum in the reservoir 1 and provide a corresponding first measuring signal. The measuring signal of the vacuum sensor 12 is supplied via a first measuring signal line 12a to the control means 6, which can carry out regulation of the vacuum taking into account this measuring value.

The control means 6 according to the first embodiment furthermore includes a display 8 which indicates to the user the set venous inflow amount and/or the set vacuum.

Figure 2:
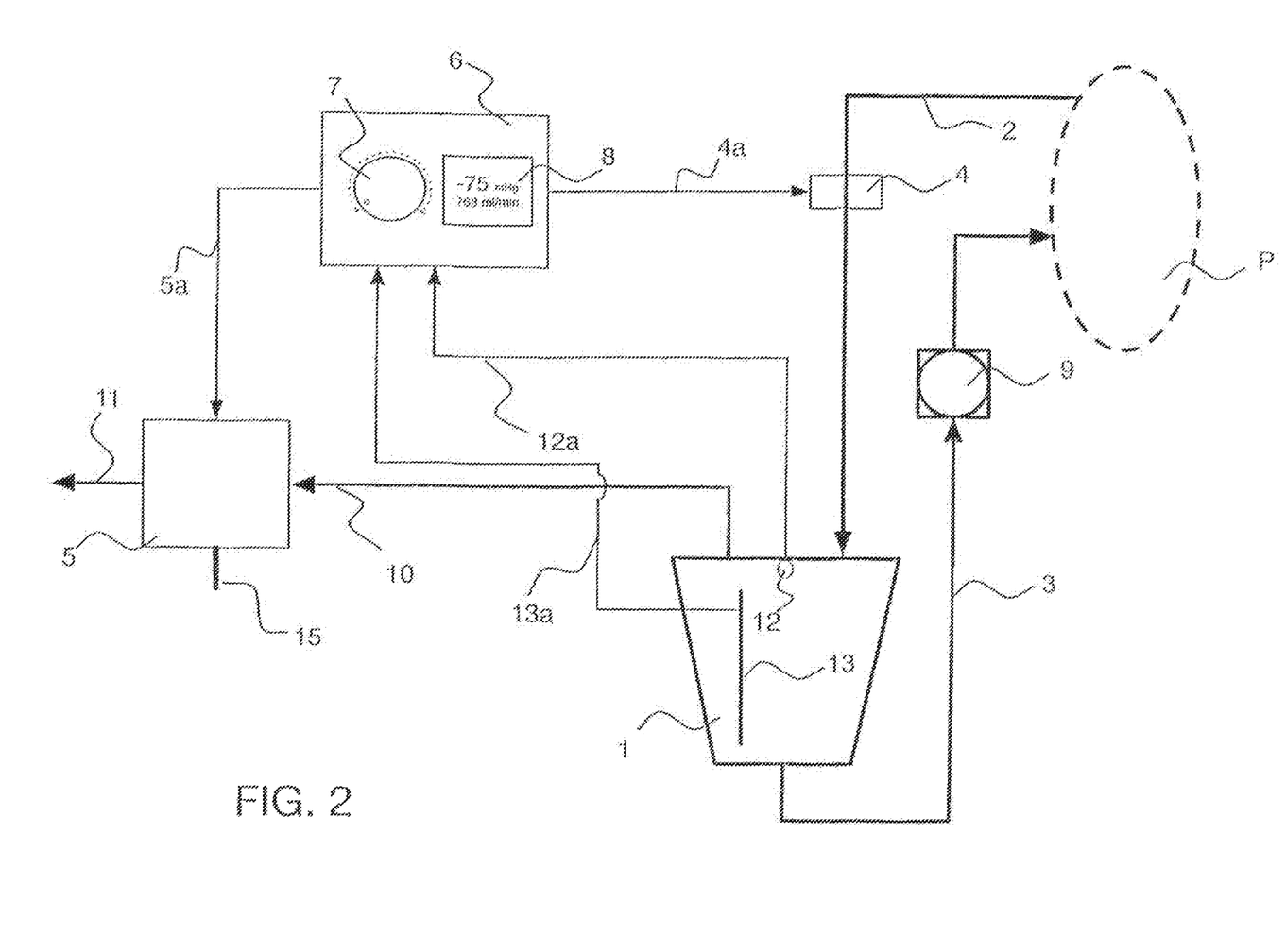
FIG. 2 shows a view of the basic structure of an extracorporeal blood circulation system having a device according to a second embodiment of the invention.

FIG. 2 shows a second embodiment of a device according to the invention, which includes all of the aspects of the first embodiment, and thus reference can be made to the description of the first embodiment in connection with FIG. 1 as regards these points. The second embodiment additionally includes a level sensor 13 that detects the level of blood actually present in the reservoir 1 and thus detects the amount of stored blood. The level sensor 13 generates a second measuring signal which is supplied to the control means 6 via a second measuring signal line 13a. With the aid of the second measuring signal, the control means 6 is able to take the amount of blood actually present in the reservoir 1 into account during vacuum regulation so as to increase the vacuum in the reservoir 1 and thus increase the venous inflow to the reservoir 1 if the level of blood in the reservoir 1 sinks below a predetermined limit. The control means 6 according to the second embodiment can furthermore monitor the reaching of a predetermined upper fill level of the reservoir 1 so as to restrict the venous inflow.

Figure 3:
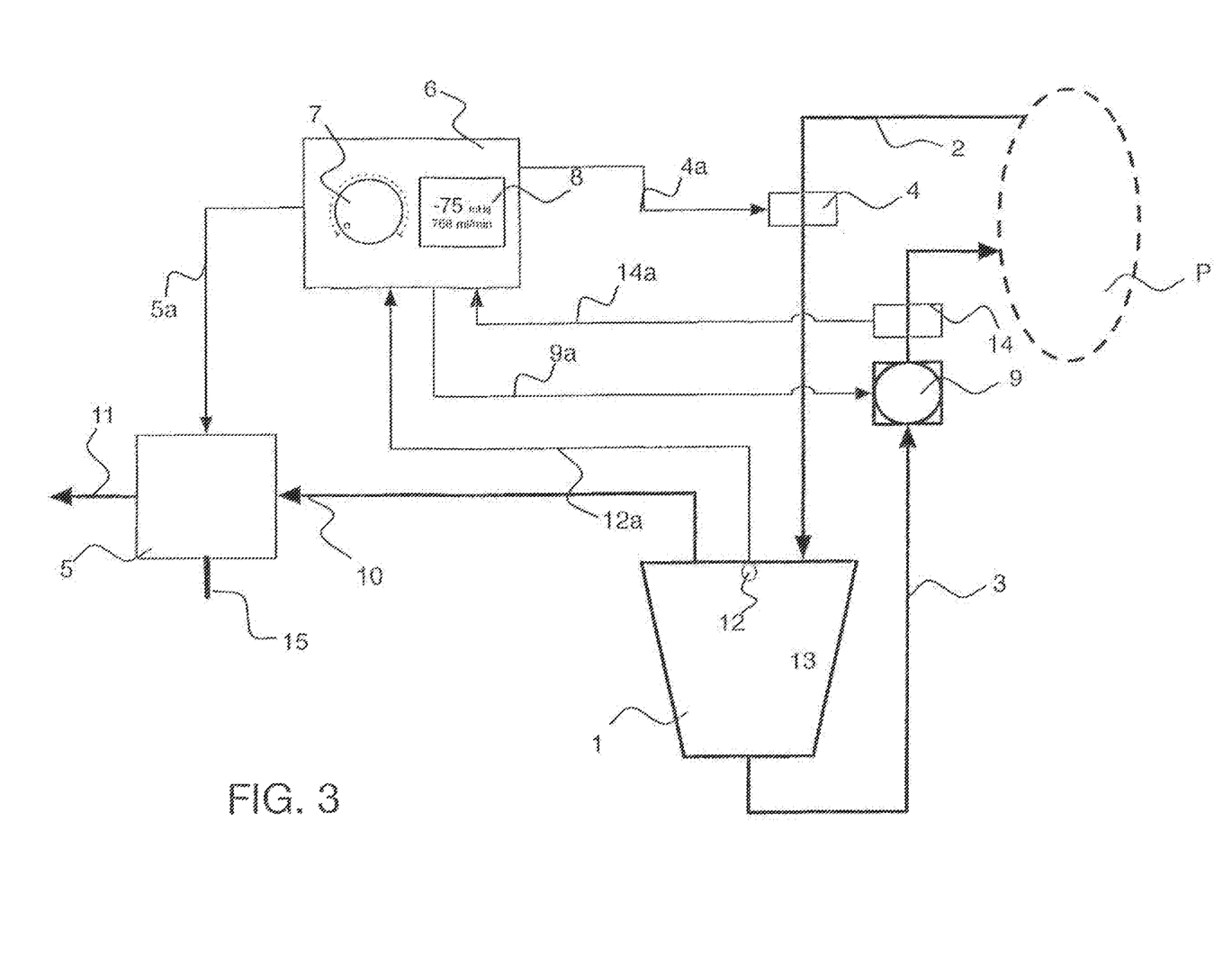
FIG. 3 shows a view of the basic structure of an extracorporeal blood circulation system having a device according to a third embodiment of the invention.

FIG. 3 shows a third embodiment of a device according to the invention, which includes all of the aspects of the first embodiment, and thus reference can be made to the description of the first embodiment in connection with FIG. 1 as regards these points. The third embodiment additionally includes an inflow amount sensor 14 that detects the arterial inflow amount and hence the amount of blood which is supplied to the patient P via the arterial inflow line 3 and is thus removed from the reservoir 1. The amount sensor 14 is arranged on the arterial inflow line 3 either downstream, as shown in FIG. 3, or upstream of the pump 9. The amount sensor 14 outputs a third measuring signal that is supplied to the control means 6 via a third measuring signal line 14a. Owing hereto, the control means 6 is able to take the amount of blood removed from the reservoir 1 into consideration during vacuum regulation and configure the venous inflow accordingly. So as to have an influence on the arterial inflow, the control means 6 in the third embodiment can output a third actuating signal to the pump 9 via a third actuation line 9a, by means of which the delivery rate of the pump is adjusted or at least influenced.

Figure 4:
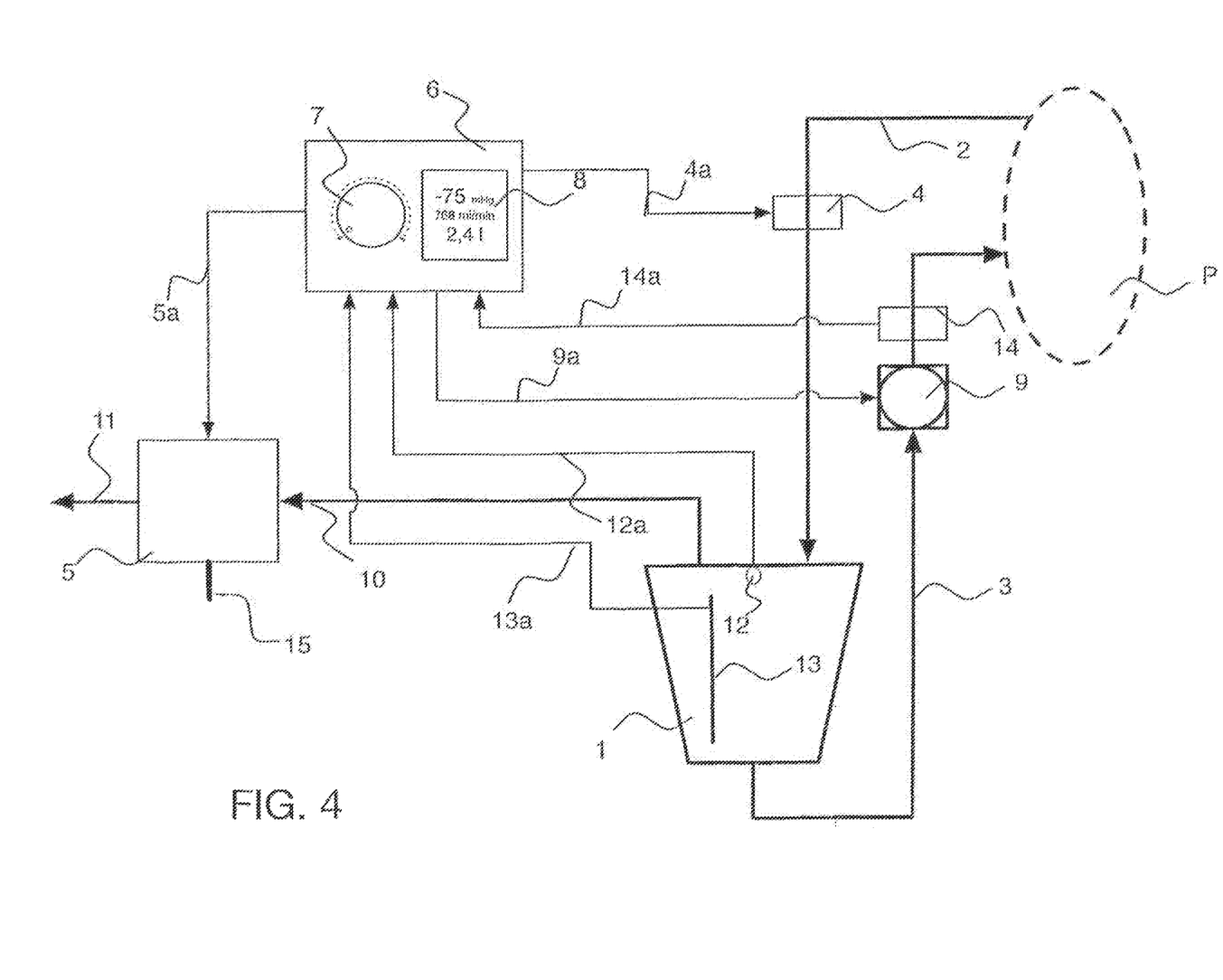
FIG. 4 shows a view of the basic structure of an extracorporeal blood circulation system having a device according to a fourth embodiment of the invention.

FIG. 4 shows a fourth embodiment of a device according to the invention, which includes all of the aspects of the first three embodiments, and thus reference can be made to the description of the first three embodiments in connection with FIGS. 1, 2 and 3 as regards these points. By combining all of the aspects of the embodiments described above, a device for establishing the venous inflow to the reservoir 1 is created, which allows an almost fully automatic control/regulation of the amount of blood stored in the reservoir 1. The reason for this is that via the gradual closure of the venous inflow line and the regulation of the vacuum in the reservoir 1, the control means 6 can set the amount of blood supplied to the reservoir 1, the current amount of which is respectively detected by the level sensor 13. The control means 6 can at the same time detect the arterial inflow amount via the amount sensor 14 and set or influence it by control of the pump 9. Accordingly, the operating element 7 of the control means 6 can also be configured in the fourth embodiment such that the amount of blood stored in the reservoir 1 is set by the user. This design is taken into consideration in FIG. 4 insofar as the actual fill level of the reservoir 1 is also shown on the display 8. On the basis of the specification of the amount of blood by the user and taking into consideration the physiological marginal conditions that ensure supply of the patient, the control means 6 then effects in a fully automatic manner the adjustment of the venous inflow to the reservoir 1 and the arterial outflow from the reservoir 1 of the extracorporeal blood circulation system.

As is shown in FIGS. 1 to 4, the vacuum unit 5 can be equipped in all of the embodiments with a safety device 15 which, upon corresponding actuation by the control means 6 or if control should fail, interrupts the application of a vacuum to the reservoir 1 and establishes atmospheric pressure in the reservoir 1.

We claim:

1. A device for establishing venous inflow to a blood reservoir of an extracorporeal blood circulation system including a venous inflow line from a patient to the blood reservoir and an arterial inflow line extending from the blood reservoir to the patient, the device comprising:
   a restricting unit configured for gradually clamping the venous inflow line in order to restrict a venous inflow amount to the blood reservoir;
   a vacuum unit configured for applying a vacuum to the blood reservoir in order to increase the venous inflow amount to the blood reservoir; and
   a control device that includes only one single operating element for setting an amount of venous inflow to the blood reservoir, the single operating element having a plurality of operating positions and configured to be manipulated in a single manipulation by a user to establish both a degree of closure of the venous inflow line and an amount of vacuum in the blood reservoir for venous inflow to the blood reservoir at, above or below a basic value established by gravitational conveyance;
   wherein, at each operating position of the plurality of operating positions, the control device is configured to supply a different combination of a restricting unit setting that corresponds to the operating position to the restricting unit for establishing the degree of closure of the venous inflow line to define an extent of a restriction of the venous inflow amount to the blood reservoir based on the manipulation of the single operating element in the single manipulation and a vacuum unit setting that corresponds to the operating position to the vacuum unit for establishing the amount of vacuum in the blood reservoir to define an extent of the increase in the venous inflow amount to the blood reservoir based on the manipulation of the single operating element in the single manipulation, without the use of a blood level sensor and blood level signals.

2. The device according to claim 1, wherein the control device further comprises a display device for visual display of a display value corresponding to the venous inflow amount.

3. The device according to claim 1, wherein the vacuum unit is connected to a vacuum source via a line.

4. The device according to claim 1, wherein the vacuum unit comprises an integrated vacuum source.

5. The device according to claim 1, further comprising a vacuum sensor for detecting a vacuum in the blood reservoir, the vacuum sensor connected to the control-device for providing a first measuring signal.

6. The device according to claim 1, further comprising an arterial inflow amount sensor for detecting an inflow amount conveyed in the arterial inflow line extending from the blood reservoir to the patient, the arterial inflow amount sensor connected to the control device for providing a third measuring signal.

7. The device according to claim 1, further comprising a blood pump, disposed along the arterial inflow line, to which a third actuating signal corresponding to a delivery rate of the blood pump established by the user is supplied by the control device to the blood pump, wherein the delivery rate controls a rate at which blood is pumped from the reservoir to the patient.

8. The device according to claim 1, wherein the single operating element is configured for specifying an amount of blood to be stored in the blood reservoir.

9. The device according to claim 1, wherein the vacuum unit further comprises a safety device configured such that, upon actuation by the control device or upon failure of the control device, an application of a vacuum to the blood reservoir is interrupted which establishes atmospheric pressure in the blood reservoir.

10. A device for establishing venous inflow to a blood reservoir of an extracorporeal blood circulation system including a venous inflow line from a patient to the blood reservoir and an arterial inflow line extending from the blood reservoir to the patient, the device comprising:
- a restricting unit configured for gradually clamping the venous inflow line in order to restrict a venous inflow amount to the blood reservoir;
- a vacuum unit configured for applying a vacuum to the blood reservoir in order to increase the venous inflow amount to the blood reservoir;
- a vacuum sensor configured for detecting a vacuum in the blood reservoir, the vacuum sensor connected to the control-device for providing a first measuring signal;
- a control device that includes only one single operating element for setting an amount of venous inflow to the blood reservoir, the single operating element having a plurality of operating positions and configured to be manipulated in a single manipulation by a user to establish both a degree of closure of the venous inflow line and an amount of vacuum in the blood reservoir for venous inflow to the blood reservoir at, above or below a basic value established by gravitational conveyance;
- a level sensor for detecting a level of blood in the blood reservoir, the level sensor connected to the control device for providing a second measuring signal; and
- an arterial inflow amount sensor for detecting an inflow amount conveyed in the arterial inflow line extending from the blood reservoir to the patient, the arterial inflow amount sensor connected to the control device for providing a third measuring signal;
- wherein, at each operating position of the plurality of operating positions, the control device is configured to supply a different combination of a restricting unit setting corresponding to the operating position to the restricting unit for establishing the degree of closure of the venous inflow line to define an extent of a restriction of the venous inflow amount to the blood reservoir based on the manipulation of the single operating element in the single manipulation and a vacuum unit setting corresponding to the operating position to the vacuum unit for establishing the amount of vacuum in the blood reservoir to define an extent of the increase in the venous inflow amount to the blood reservoir based on the manipulation of the single operating element in the single manipulation.

11. The device according to claim 10, wherein the control device further comprises a display device for visual display of a display value corresponding to the venous inflow amount.

12. The device according to claim 10, wherein the vacuum unit is connected to a vacuum source via a line.

13. The device according to claim 10, wherein the vacuum unit comprises an integrated vacuum source.

14. The device according to claim 10, further comprising a blood pump, disposed along the arterial inflow line, to which a third actuating signal corresponding to a delivery rate of the blood pump established by the user is supplied by the control device to the blood pump, wherein the delivery rate controls a rate at which blood is pumped from the reservoir to the patient.

15. The device according to claim 10, wherein the single operating element is configured for specifying an amount of blood to be stored in the blood reservoir.

16. The device according to claim 10, wherein the vacuum unit further comprises a safety device configured such that, upon actuation by the control device or upon failure of the control device, an application of a vacuum to the blood reservoir is interrupted which establishes atmospheric pressure in the blood reservoir.

* * * * *